United States Patent [19]

Stahl

[11] 4,303,063

[45] Dec. 1, 1981

[54] OCULAR MASSAGE DEVICE

[76] Inventor: Norman O. Stahl, 3199 Monterey Dr., Merrick, N.Y. 11566

[21] Appl. No.: 127,596

[22] Filed: Mar. 6, 1980

[51] Int. Cl.³ .................... A61H 1/02; A61F 13/12
[52] U.S. Cl. ........................... 128/25 A; 128/163
[58] Field of Search ............... 128/645, 648, 650–652, 128/676–678, 684–686, 774, 25 A, 76.5, 160, 163, 327

[56] References Cited

U.S. PATENT DOCUMENTS

| | | | |
|---|---|---|---|
| 2,690,173 | 9/1954 | Seeger et al. | 128/25 A |
| 3,713,446 | 1/1973 | Sarnoff | 128/327 |
| 3,929,129 | 12/1975 | Archambault | 128/327 |
| 4,175,562 | 11/1979 | Honan | 128/163 |
| 4,193,401 | 3/1980 | Marinello | 128/163 |

*Primary Examiner*—C. Fred Rosenbaum
*Attorney, Agent, or Firm*—Albert F. Kronman

[57] ABSTRACT

An ocular massage device comprising a rigid curved plate to rest upon the forehead and cheek and overlie the eye of the patient. An inflatable member between the plate and the patient's eyelid. An inlet tube to admit fluid under the pressure into the inflatable member, an outlet tube to permit fluid to leave the inflatable member, a check valve on the outlet tube to release fluid exceeding a desired pressure from the inflatable member and a second inflatable member to receive fluid from the check valve.

6 Claims, 4 Drawing Figures

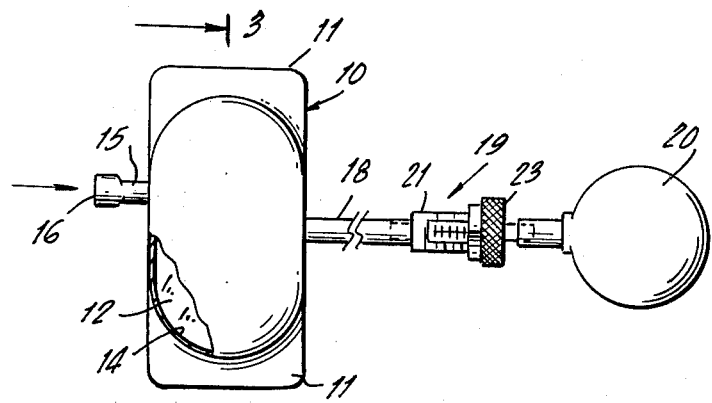
FIG. 1
FIG. 3
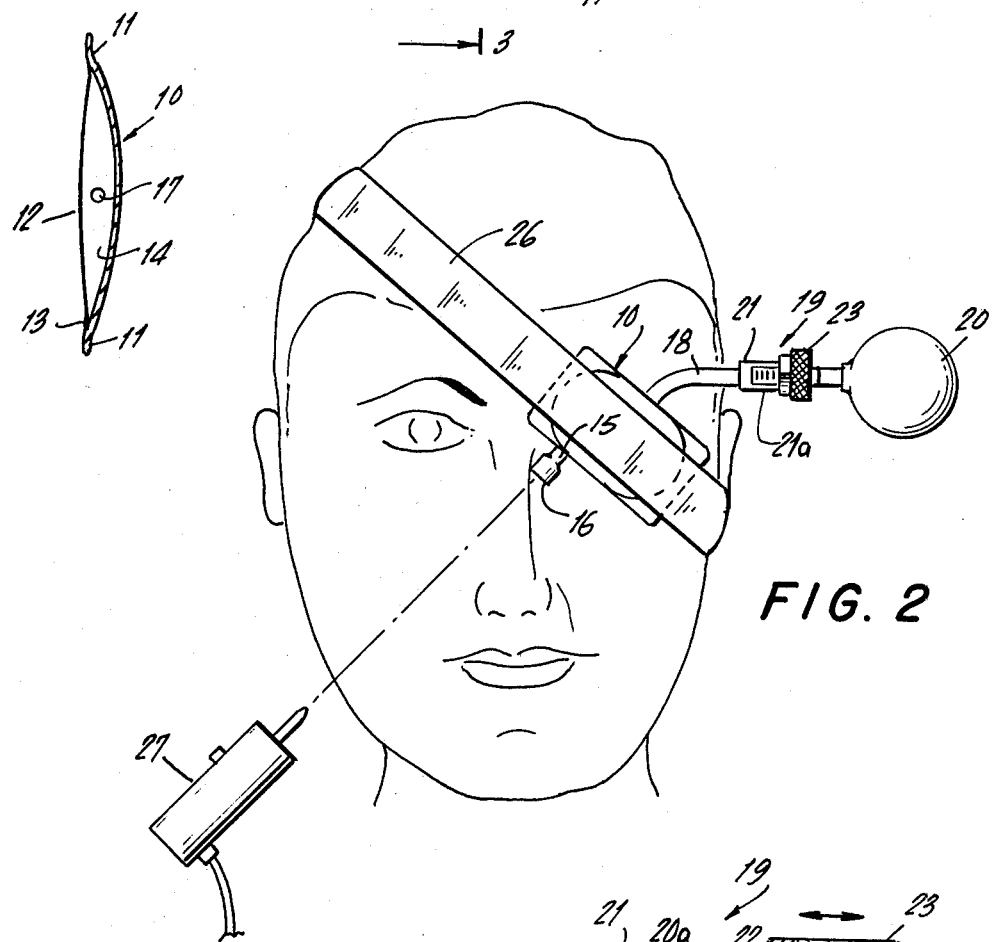
FIG. 2
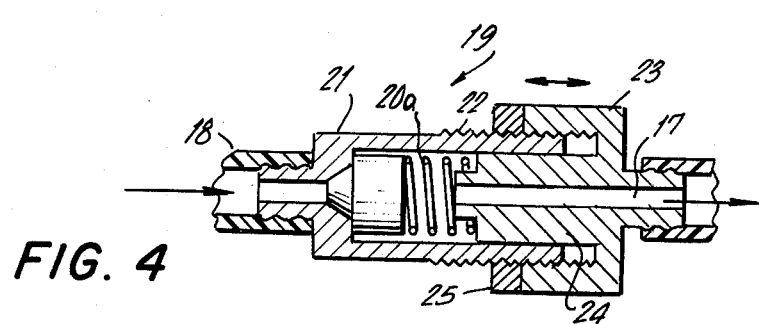
FIG. 4

OCULAR MASSAGE DEVICE

BACKGROUND OF THE INVENTION

Ocular Massage is an important procedure in preoperative management of a patient prior to intra-ocular surgery. The massage serves to "soften the eye" so that when the eye is opened there is a markedly reduced tendency toward expulsion of the internal ocular contents.

Ocular massage is usually carried out by means of various degrees of compression to the eye through the closed eyelids. Such treatment is usually provided by intermittent finger or palm compression. The result is that the amount of compression applied varies from operator to operator and from time to time so that there is no standard amount employed. It has been attempted to place a sponge rubber ball on the patients closed eye and, holding it in place with an elastic band, to provide the effect of ocular massage. Here again, there is no standard amount of compression since prominent eyes receive more pressure than deep set eyes.

Another prior art device employs a diaphragm on the eyelids held in place by a strap around the patient's head, a Sphygmomanometer then is employed to inflate the diaphragm to a pressure of between 30–40 mm. of mercury. Such an instrument is difficult to control and should someone accidentally raise the pressure on the eye to a very high level, if it remains at that level, potentially serious and permanent damage to the eye may occur.

Accordingly, it is the object of the present invention to provide an ocular message device in which the amount of pressure applied to the patient's eye can be carefully regulated.

Another object of the present invention is to provide an eye massage device which is easy to apply, will remain in place, and is of inexpensive construction.

A further object of the present invention is to provide an ocular massage device in which the amount of pressure can be preset before application to the patient's eye.

SUMMARY

An ocular massage device according to the present invention consists of a rigid curved plate which extends from the forehead to the cheek of the patient and forms a chamber over the eye. An inflatable diaphragm or balloon is secured to the plate between the plate and the patient's eye. The diaphragm is provided with means for inflating it by a source of outside fluid under pressure so that the diaphragm will press against the eyelid of the patient. The curved plate and diaphragm are held against the patient's face by means of a strap secured about the patient's head. An exit port leads from the diaphragm or balloon and is connected by means of tubing to a check valve. The check valve is spring loaded and the spring tension can be controlled to precisely regulate the amount of air pressure within the diaphragm during ocular massage. A second balloon is secured to the outlet side of the check valve to receive excess fluid from the check valve.

DESCRIPTION OF THE DRAWINGS

In the accompanying drawing forming part hereof;

FIG. 1 is a somewhat diagrammatic view partly in section of a complete embodiment of the present invention.

FIG. 2 is a pictorial view of a patient's head with the ocular massage device of the present invention in place.

FIG. 3 is a cross sectional view taken on line 3—3 of FIG. 1 looking in the direction of the arrows of the plate and diaphragm assembly.

FIG. 4 is a check valve useful in the present invention.

DETAILED DESCRIPTION

Referring to the drawings and particularly FIGS. 1, 2, and 3; 10 indicates a rigid curved plate made of metal, plastic or the like. The plate is provided with flanges 11 at the top and bottom thereof which are adapted to rest upon the cheek and forehead of the patient when the device is placed over the eye. A thin elastomeric sheet 12 hereinafter referred to as the diaphragm is bonded at its edges 13 to the curved plate 10 as best shown in FIG. 3. In this manner, a fluid-tight chamber 14 is provided between the diaphragm 12 and the curved plate 10. A valve stem 15 (best shown in FIGS. 1 and 2) is secured to the diaphragm 12 in communication with the chamber 14. The inlet portion 16 of the valve stem is provided with a port which is self sealing and through which gas or liquid under pressure may be injected.

An outlet port 17 is also provided in the diaphragm to receive flexible tubing 18 which is thus in communication with the chamber 14. A small check valve 19 is connected between the tubing 18 and an inflatable balloon 20.

As shown in greater detail in FIG. 4, the check valve 19 is spring loaded by the coil spring 20a. The housing 21 of the check valve is threaded as shown at 22 to receive an adjusting thimble 23. The thimble is internally threaded to receive the external threads 22. A central boss 24 in the thimble 23 bears against the coil spring 20a. By rotating the thimble 23 the tension on the spring 20a may be regulated as desired. A locking nut 25 is also threaded upon the housing threads 22 and may be employed to prevent accidental movement of the thimble 23.

By reference to FIG. 2 and the above description the operation of the present device will be apparent as follows:

The curved plate 10 is secured to the head of the patient by means of a band 26 which may be of some suitable elastomeric material. A source of fluid under pressure is applied by means of a suitable device 27 to the valve 16 thereby filing the chamber 14 and distending the diaphragm 12 against the patient's eyelid. The check valve 19 is preset to a desired ocular pressure by rotating the thimble 23 to a desired point upon the threads 22. Suitable indicia 21a may be provided for this purpose. When the fluid pressure exceeds the tension of the spring 20a upon the valve plunger 28, fluid will be released into the balloon 20 causing it to inflate, warning the operator to remove the fluid source. The ocular massage device is then operable.

The normal movement of the patient's eye beneath the eyelid will furnish the necessary massaging action to bring about the softening of the eye.

In order to release the pressure of the diaphragm on the eye, the thimble 23 may be backed off on the threads 22 to reduce the tension on the spring 20a so that the fluid can escape through the check valve 19.

Having thus fully described the invention, what is claimed as new and desired to be secured by Letters Patent of the United States is:

1. An ocular massage device for attachment to the head of a patient comprising a rigid plate, a curved portion on said plate, a first inflatable member carried by the plate to overlie the eye of the patient, an entrance port for the first inflatable member to direct fluid under pressure into the said inflatable member, an exit port on the first inflatable member to direct fluid out of the inflatable member, a first and a second valve means connected to the entrance and exit ports to control the fluid pressure in the first inflatable member, a second inflatable member coupled to the exit port of the second value means to receive fluid from the said valve means and means to secure the plate to the head of the patient over the eye to be treated.

2. A device according to claim 1 in which the plate is provided with opposed flanges spaced to rest upon the forehead and cheek of the patient.

3. A device according to claim 1 in which the inflatable member is a diaphragm bonded at its edges to the plate to form a chamber with said plate.

4. A device according to claim 1 in which the first and second valve means are check valves.

5. A device according to claim 4 in which the second valve is spring loaded and the spring is variably tensioned by a thimble carried upon the valve.

6. A device according to claim 6 in which the valve is provided with indicia and the thimble is adjustably carried upon the valve with respect to the indicia so that the spring tension may be pre-set to any desired fluid pressure.

* * * * *